United States Patent
Ray et al.

(10) Patent No.: US 6,201,153 B1
(45) Date of Patent: Mar. 13, 2001

(54) SYNTHESIS OF MIDODRINE HCl FROM A NOVEL INTERMEDIATE 1-(2',5'-DIMETHOXYPHENYL)-2-AZIDOETHANONE

(75) Inventors: Anup K. Ray, Staten Island, NY (US); Hiren Patel, Edison; Mahendra R. Patel, East Brunswick, both of NJ (US)

(73) Assignee: Geneva Pharmaceuticals Inc., Broomfield, CO (US)

( * ) Notice: Subject to any disclaimer, the term of this patent is extended or adjusted under 35 U.S.C. 154(b) by 0 days.

(21) Appl. No.: 09/550,417

(22) Filed: Apr. 17, 2000

(51) Int. Cl.⁷ .................................................. C07C 233/00
(52) U.S. Cl. ............................................. 564/196; 552/10
(58) Field of Search ................................. 552/10; 504/196

(56) References Cited

U.S. PATENT DOCUMENTS 3,340,298    9/1967   Wismayr et al. .................... 260/562

FOREIGN PATENT DOCUMENTS 241435    7/1965   (AT) .

OTHER PUBLICATIONS

Rammler et al., "Studies on Polynucleotides. XX. Amino Acid Acceptor Ribonucleic Acids. The Synthesis and Properties of 2'(or 3'))–O–(DL–Phenylalanyl)–adeonsine, 2'(or 3')–O–(DL–Phenylalanyl)–uridine and Related Compounds", J. Am. Chem. Soc., vol. 85, p. 1997–2002 (1963).

Jonas et al., "The Use of Midodrin in the Treatment of Ejaculation Disorders following Retroperitoneal Lymphadenectomy", Eur. Urol., vol. 5, pp. 184–187 (1979).

Soai et al., "Reduction of Azides to Amines with Sodium Borohydride in Tetrahydrofuran with Dropwise Addition of Methanol", Synth. Commun., pp. 48–49, (1986).

Primary Examiner—Samuel Barts
(74) Attorney, Agent, or Firm—Lydia T. McNally

(57) ABSTRACT

Midodrine hydrochloride, ±1-(2',5'-dimethoxyphenyl)-2-glycineamido-ethanol-(1)-HCl, is prepared from a novel intermediate, 1-(2',5'-dimethoxyphenyl)-2-azidoethanone.

8 Claims, No Drawings

SYNTHESIS OF MIDODRINE HCl FROM A NOVEL INTERMEDIATE 1-(2',5'-DIMETHOXYPHENYL)-2-AZIDOETHANONE

BACKGROUND OF THE INVENTION

The present invention relates to the synthesis of midodrine hydrochloride, ±1-(2',5'-dimethoxyphenyl)-2-glycineamido-ethanol-(1)-HCl, from a novel intermediate, 1-(2',5'-dimethoxyphenyl)-2-azidoethanone.

The compound midodrine is part of the class of compounds known as phenylalkanolamine derivatives which have been found to be effective in treating hypertensive conditions due to their long lasting blood pressure increasing effect.

SUMMARY OF THE INVENTION

The objective of the present disclosure is to provide novel synthetic strategies to prepare midodrine HCl from a novel intermediate, 1-(2',5'-dimethoxyphenyl)-2-azidoethanone. The synthetic routes of the present invention provide increased yields and minimized by-products, which therefore also minimizes expenses.

DETAILED DESCRIPTION OF THE INVENTION

The present invention relates to the synthesis of midodrine hydrochloride, ±1-(2',5'-dimethoxyphenyl)-2-glycineamido-ethanol-(1)-HCl. The synthetic route comprises reduction of the intermediate, 1-(2',5'-dimethoxyphenyl)-2-azidoethanone (Compound II) to produce the compound ±1-(2',5'-dimethoxyphenyl)-2-glycineamido-ethanol-(1)-HCl (Compound I).

The novel intermediate, 1-(2',5'-dimethoxyphenyl)-2-azidoethanone (Compound II) is prepared by acylating the compound 1,4-dimethoxybenzene (Compound III) by a Friedel-Crafts reaction with haloacetylchloride or haloaceticanhydride and anhydrous aluminum chloride in the presence of a chlorinated organic solvent. Halo includes chloro, bromo, and the like. Examples of haloacetylchlorides include chloroacetylchloride and bromoacetylchlorides. Examples of haloacetic anhydrides include chloro-acetic anhydride and bromo-acetic anhdyride. Examples of chlorinated organic solvents are methylenechloride and dichloroethane. Carbon disulfide may also be used as a solvent. The product, 1-(2',5'-dimethoxyphenyl)-2-haloethanone (Compound IV), is obtained in pure form; only one isomer is obtained as all the four positions of benzene nucleus are equivalent. This step is shown schematically as follows, with X representing halo, preferably chloro:

Step 1

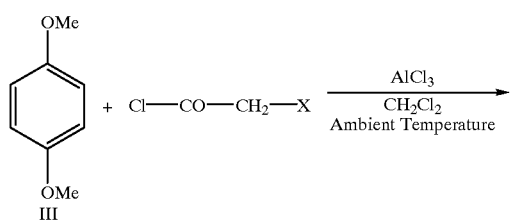

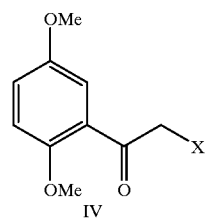

The intermediate, Compound II, is prepared by introducing an azide group to replace halo from the α-position in Compound IV. The halogen containing carbon is highly activated by the presence of the adjacent carbonyl group and is therefore easily replaced. This reaction is carried out in nitrogen purged 60% acetone-water mixture. This step is shown schematically as follows:

Step 2

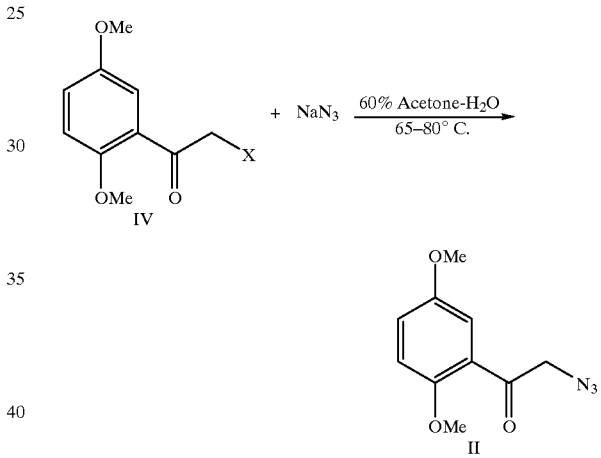

This novel ketoazide compound, 1-(2',5'-dimethoxyphenyl)-2-azidoethanone (Compound II), is used as an intermediate for the synthesis of 1-(2',5'-dimethoxyphenyl)-2-glycineamidoethanol-(1) HCl (Compound I).

The introduction of the azido group into Compound II allows the carbonyl and the azide to be reduced simultaneously in one pot. This provides an improvement to the process in that fewer process steps are needed. Therefore in the next step, the keto and the azide groups are both reduced to produce ±1-(2',5'-dimethoxyphenyl)-2-aminoethanol (Compound V), a known metabolite of midodrine. The reduction may be by any known method using known reducing agents including reduction by lithium aluminum hydride (LiAlH$_4$) in tetrahydrofuran, or reduction by sodium borohydride in tetrahydrofuran or a mixture of tetrahydrofuran and methanol, or by hydrogenation in the presence of Pd/C (10%) with methanol, ethanol or a mixture of organic solvents. This reaction step is shown as follows:

Step 3

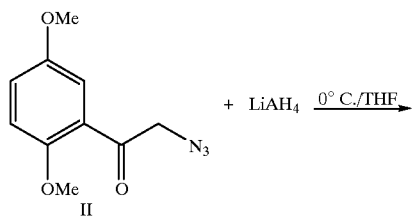

20

In conventional amidation reactions, the aminoethanol, Compound V, produced in the above step may be reacted with N-carbo-t-butoxyglycine-amido (N-BOC-Glycine) in the presence of dicyclohexylcarbodiimide (DCC) to form an amide bond. However, if DCC is used simultaneously with aminoethanol, Compound V, and N-BOC-Glycine in situ, the yield is poor due to the generation of by-products. Moreover, one of the by-products, dicyclohexylurea, DCU, becomes trapped and remains in the product.

It has been found, in accordance with the present invention, that this problem with DCU could be avoided. In the synthetic reaction of the present invention a pure anhydride was synthesized by reacting N-BOC-glycine with DCC, in a 2:1 ratio, in dry methylene chloride. The DCU thus formed is precipitated out at 0° C. to provide exclusively N-BOC-glycine anhydride, Compound VI, in the solution. The pure anhydride was thus obtained:

Step 4

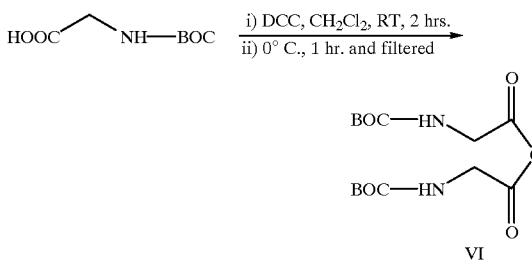

In the above reaction scheme, RT signifies ambient temperature.

The anhydride produced according to Step 4, Compound VI, was then reacted with the amine group of the aminoalcohol, Compound V, in the presence of 4,4'-dimethylaminopryidine, DMAP, a catalyst found to be very effective in reducing the reaction time and increasing the yield of the product, 1-(2',5'-dimethoxyphenyl)-2-(N-carbo-t-butoxyglycine-amido)-ethanol-(1), Compound VII.

Step 5

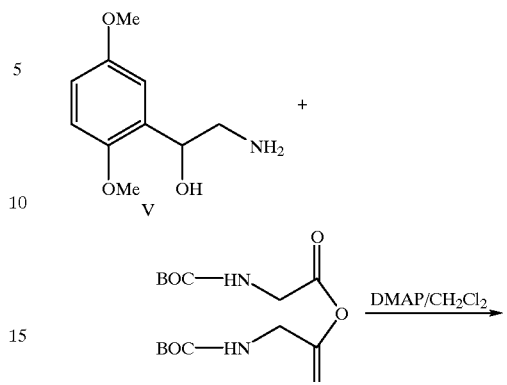

The 1-(2',5'-dimethoxyphenyl)-2-(N-carbo-t-butoxyglycine-amido)-ethanol-(1) compound, Compound VII, produced in Step 5 is subjected to any polar protic or aprotic solvent to yield the desired ±1-(2',5'-dimethoxyphenyl)-2-glycineamido-ethanol-(1)-hydrochloride, Compound I. Examples of polar protic or aprotic solvents include acetone/aq. HCl or HCl gas/MeOH or 3M HCl—EtOAc.

Step 6

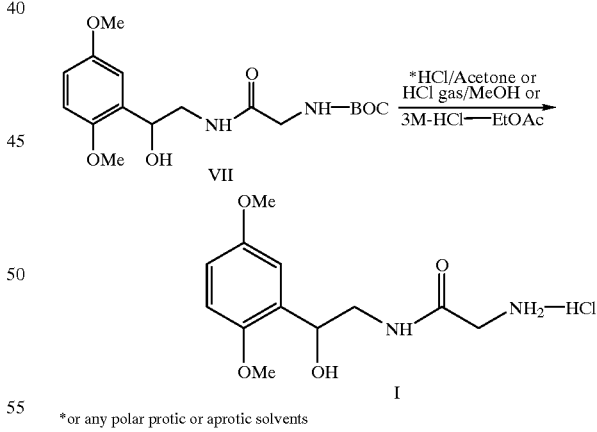

*or any polar protic or aprotic solvents

The following examples are merely illustrative and not intended to limit the scope of the present invention in any manner.

Numbering of -N-BOC (Compound VII) and the final product (Compound I) have been assigned as shown below. This numbering has been followed for assigning the protons in the $^1$H-NMR interpretation of all the synthesized molecules.

1-(2',5'-dimethoxyphenyl)-2-(N-Carbo-t-butoxyglycine-amido)-ethanol-(1)
Compound VII:

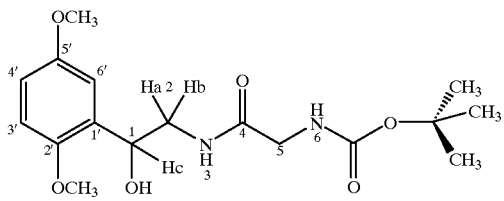

±1-(2',5'-dimethoxyphenyl)-2-glycineamido-ethanol-(1)-hydrochloride
Compound I:

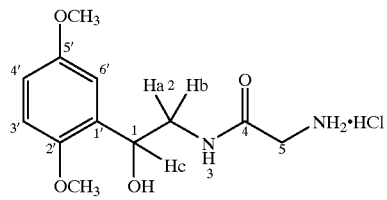

EXAMPLE 1A

Synthesis of 1-(2',5'-dimethoxyphenyl)-2-chloroethanone (Compound IV):

In a three-neck round bottom 2 liter flask, 60.0 g (0.434 mol) of 1,4-dimethoxybenzene is added. To the flask is added 300 mL dry dichloromethane to dissolve the solid. When the solution is clear, 63.7 g (0.477 mol) of anhydrous $AlCl_3$ is added through a powder funnel and the funnel is washed with dichloromethane. The resulting solution is yellowish in color. This solution is stirred at room temperature for 5 minutes and 40.0 mL (0.50 mol) chloroacetylchloride in 5 mL dichloromethane is added dropwise (total addition time 1 hour 30 minutes) and is stirred vigorously at room temperature. The color of the solution became is orange-red and then like red wine. The solution is stirred for 4 hours after addition at room temperature and then poured in to a mixture of crushed ice and 126 mL conc. HCl and stirred for 20 minutes again. The organic phase is separated and the aqueous phase is extracted with $CH_2Cl_2$ (100 mL×3). Total dichloromethane fractions are combined and washed with $H_2O$ (100 mL×2), cold 10% aq. NaOH (200 mL×1) and $H_2O$ (100 mL×2) and dried over anhydrous sodium sulfate. The organic phase is evaporated under reduced pressure and the thick solution is cooled to room temperature yielding a yellow solid (59.0 g, yield 64%). The crude product is crystallized from methanol (m.p. 89–91° C.).

EXAMPLE 1B

The procedure described in Example 1A is repeated utilizing chloroacetic anhydride under refluxing conditions instead of chloroacetylchloride. The compound 1-(2',5'-dimethoxyphenyl)-2-chloroethanone is obtained as a light grey solid with the same yield. The following physical properties are measured:

m.p. 89–91° C. (dec)

MS (El-MS): m/z 214 (M$^+$)

$^1$H-NMR (CDCl$_3$): δ (ppm): 3.80 (3H, s, 2'-OCH$_3$), 3.90 (3H, s, 5'-OCH$_3$), 4.80 (2H, s, 2-CH$_2$), 6.9 (1H, o-d, J=9.2 Hz, 3'-H), 7.10 (1H, o,m-dd, J=3.2, 9.2 Hz, 4'-H), 7.40 (1H, m-d, J=3.2Hz, 6'-H).

EXAMPLE 2

Synthesis of 1-(2',5'-dimethoxyphenyl)-2-azidoethanone (Compound II):

In a 200 mL round bottom flask, 6.0 g (0.028 mol) of 1-(2',5'-dimethoxyphenyl)-2-chloroethanone prepared according to Example 1A and 3.27 g (0.0504 mol) of sodium azide are charged and 25 mL 60% (v/v) Acetone-Water mixture is added. (Before addition, the acetone-water mixture is purged with nitrogen gas). The solution is heated in a water bath (65–80° C.) for 3 hours and 30 minutes under nitrogen atmosphere. After the reaction, acetone is distilled off under reduced pressure resulting in a lump of solid. To the solid, 10 mL water is added. The aqueous part is extracted with dichloromethane (30 mL×3) and washed with 5% cold aqueous NaOH solution (20 mL×1) and saturated brine water (10 mL×2). The aqueous part is dried over anhydrous sodium sulfate, and the solution is treated with 500 mg activated carbon. The mixture is warmed to 30° C. with a water bath under nitrogen atmosphere and stirred for 20 minutes. The solution is filtered and concentrated under reduced pressure. The thick yellow colored solution, is cooled to room temperature to yield a light yellow color solid which is dried in the vacuum desiccator over $P_2O_5$ (5.0 g, yield 82%). The solid is crystallized from methanol. The following physical properties are measured:

m.p. 92–93° C. (dec)

MS (El-MS): m/z 221 (M$^+$)

$^1$H-NMR (CDCl$_3$): δ (ppm): 3.80 (3H, s, 2'-OCH$_3$), 3.92 (3H, s, 5'-OCH$_3$), 4.53 (2H, s, 2-CH$_2$), 6.93 (1H, o-d, J=9.1 Hz, 3'-H), 7.12 (1H, o,m-dd, J=3.1, 9.1 Hz, 4'-H), 7.45 (1H, m-d, J=3.1 Hz, 6'-H).

EXAMPLE 3

Synthesis of ±1-(2',5'-dimethoxyphenyl)-2-aminoethanol (Compound V):

10.12 g (0.0458 mol) of 1-(2',5'-dimethoxyphenyl)-2-azideethanone, prepared according to Example 2, is taken in 40 ml of dry THF. The solution is cooled to 0° C. To this solution, 45 ml (0.045 mol) LAH (1 M in THF) solution is added dropwise. The mixture is stirred at 0° C. for 45 minutes. To this solution, saturated $Na_2SO_4$ solution (25–26 ml) is added dropwise at 0° C. After this addition the brown color solution with white precipitate is stirred for 25 minutes and filtered on vacuum pump washing the solid with dry THF. The filtrate is washed with saturated brine water and dried over $Na_2SO_4$. Then the filtrate is treated with activated carbon with warmth under nitrogen. The solution is filtered on vacuum pump and distilled under reduced pressure at temperature 60° C. A brown liquid is obtained and when blown with nitrogen a solid appears. This solid is triturated twice with n-hexane (10 ml×2). The resultant solid is orange-yellow and is kept under vacuum desiccator over $P_2O_5$ (6.3g, yield 70%). The solid is crystallized from ethylacetate resulting in a white powdery solid (m.p. 128–130° C.). The following physical properties are measured:

m.p. 128–130° C. (dec)

MS (El-MS): m/z 197 (M$^+$)

$^1$H-NMR (CDCl$_3$): δ (ppm): 2.8 (1H, dd, J=5.2, 12.5 Hz, 2-H$_b$, anti to H$_c$), 3.0 (1H, dd, J=3.1, 12.5 Hz, 2-H$_a$, syn to H$_c$), 4.85 (1H, q, 1-H$_c$), 6.76 (1H, dd, J=2.8, 7.5 Hz, 4'-H), 6.8 (1H, o-d, J=7.5 Hz, 3'-H), 7.0 (1H, m-d, J=2.8 Hz, 6'-H).

EXAMPLE 4
Synthesis of (±) 1-(2',5'-dimethoxyphenyl)-2-(N-Carbo-t-butoxyglycine-amido)-ethanol-(1) (Compound VII):

1.18 g (0.0057 mol) of dicyclohexyl carbodiimide (DCC) is dissolved in 15 ml of dry $CH_2Cl_2$ and 2.0 g (0.0114 mol) glycine-HN-BOC is added and dissolved. A clear solution is obtained immediately after addition and after 2–3 minutes white precipitate forms. Stirring is continued for another 2 hours at room temperature and then the mixture is kept in the freezer for 1 hour. The obtained white solid is filtered through cotton-plug-funnel while the solution is cool. The filtrate is collected in a 100 ml round bottom flask. After filtration the white solid is washed with chilled $CH_2Cl_2$. To the filtrate a catalytic amount of DMAP (2%) is added. 1.012 g (0.00513 mol) ±1-(2',5'-dimethoxyphenyl)-2-aminoethanolare added to the round-bottomed flask containing filtrate with vigorous stirring. The color of the solution becomes very light green (transparent). Stirring is continued for 2½ hours. After the reaction the solution is washed with aqueous 5% $KHSO_4$ (5 mL×2), 5% aqueous $NaHCO_3$ (5 mL×2) and $H_2O$ (5 mL×2). After washings with $H_2O$, the solution is dried over $Na_2SO_4$. The filtrate is evaporated under reduced pressure resulting in a light green syrupy liquid (1.45 g, yield 80%). On cooling at room temperature if any solid is found in the syrupy liquid the residue should be triturated with ether. White solid thus obtained is filtered and on evaporation, the ether part results in a syrupy light green liquid. The following physical properties are measured:

MS (El-MS): m/z 354 ($M^+$)

$^1$H-NMR ($CDCl_3$): δ (ppm): 1.48 (9H, s, t-butyl), 3.5 (2H, dd, two closely spaced doublet, 5-H), 3.72 (2H, m, 2-$H_a$, $H_b$), 3.75 (3H, s, 2'-$OCH_3$), 3.78 (3H, s, 5'-$OCH_3$), 5.0 (1H, q, 1-$H_c$), 6.8 (2H, m, 3',4'-H), 7.0 (1H, m-d, J=2.8 Hz, 6'-H).

EXAMPLE 5
Synthesis of ±1-(2',5'-dimethoxyphenyl)-2-glycineamido-ethanol-(1)-hydrochloride (Compound I) by aqueous HCl and Acetone:

In a 50.0 mL round bottom flask, 1.65 g (4.66 mmol) of 1-(2',5'-dimethoxyphenyl)-2-glycineamido-N-BOC prepared according to Example 4 is added and dissolved in 15 mL acetone. To this solution is added 0.4 mL conc. HCl (0.42 mL, 5.1 mmol, 37% assay, 0.38 mL is equivalent to 4.66 mmol). The mixture is stirred at 45–50° C. for 1 hr. 30 min. to 2.0 hr. The course of the reaction is monitored by HPLC. After the reaction, the mixture is allowed to cool at room temperature and the solid is filtered and washed with acetone (0.8035 g). The filtrate is heated to reduce the acetone content and cooled to room temperature to obtain the second crop of solid (0.150 g). Total weight of the solid collected is 1.012 g. HPLC is used to find out the percentage of the drug substance in the reaction mixture (filtrate). Total crude yield is between 80–85% after collection of all crops. The solid is crystallized from methanol (m.p. 190–191° C.).

EXAMPLE 6
Synthesis of ±1-(2',5'-dimethoxyphenyl)-2-glycineamido-ethanol-(1)-hydrochloride (Compound I) by HCl gas and Methanol:

In dry 20.0 mL saturated solution of HCl gas in methanol (0.82 N, determined by titration) is dissolved 1.65 g (4.66 mmol) of 1-(2',5'-dimethoxyphenyl)-2-glycineamido-N-BOC prepared according to Example 4. After stirring for about one hour at room temperature the mixture is stirred at 40–45° C. for 10 hours. The course of reaction is monitored by HPLC. Methanol after evaporation at reduced pressure, the residue is taken in 5 mL isopropyl alcohol and the mixture is cooled to 15° C. and to it is added 40–50 mL n-hexane to precipitate out the solid (0.754 g, yield 58%). The solid is crystallized from methanol (m.p. 191–192° C.).

EXAMPLE 7
Synthesis of +1-(2',5'-dimethoxyphenyl)-2-glycineamido-ethanol-(1)-hydrochloride (Compound I) by 3M HCl—EtOAc:

In 15 mL 3M-HCl—EtOAc, 2.75 g (7.76 mmol) of 1-(2',5'-dimethoxyphenyl)-2-glycineamido-N-BOC prepared according to Example 4 is dissolved. After stirring for about 45 minutes at room temperature the ethylacetate is evaporated under reduced pressure at 50° C. The solid is taken in 25 mL ether and stirred for 20 minutes. The white solid is filtered and air dried (1.92 g, 87% yield). HPLC purity is found to be 99.5%. The solid is crystallized from methanol. The following physical properties are measured:

m.p 191–192° C. (dec)

MS (El-MS): m/z 254 ($M^+$)

$^1$H-NMR ($CDCl_3$): δ (ppm): 3.39 (1H, dd, J=5.5, 16.5 Hz, 2-Hb, anti to $H_c$), 3.55 (1H, dd, J=3.6, 16.5 Hz, 2-$H_a$, syn to $H_c$), 3.66 (2H, two closely spaced doublet, 5-H), 3.73 (3H, s, 2'-$OCH_3$), 3.78 (3H, s, 5-$OCH_3$), 5.09 (1H, q, 1-$H_c$), 6.8 (1H, o-m double doublet, J=3.1, 8.2 Hz, 4'-H), 6.88 (1H, o-d, J=8.2 Hz, 3'-H), 7.05 (1 H, m-d, J=2.8 Hz, 6'-H).

We claim:

1. A method for the synthesis of ±1-(2',5'-dimethoxyphenyl)-2-glycineamido-ethanol-(1)-HCl from 1-(2',5'-dimethoxyphenyl)-2-azidoethanone comprising reduction of 1-(2',5'-dimethoxyphenyl)-2-azidoethanone with reducing agents.

2. A method according to claim 1 wherein the reducing agents are selected from the group consisting of lithium aluminum hydride, sodium borohydride and Pd/C (10%) catalyst.

3. A method for the synthesis of 1-(2',5'-dimethoxyphenyl)-2-azidoethanone comprising
   (a) acylating 1,4-dimethoxybenzene with haloacetylchloride or haloacetic anhydride and anhydrous aluminum chloride in the presence of a chlorinated solvent, and
   (b) reacting the product of step (a) with sodium azide to substitute the halogen with an azide group.

4. A method for the synthesis of ±1-(2',5'-dimethoxyphenyl)-2-glycineamido-ethanol-(1)-HCl from 1-(2',5'-dimethoxyphenyl)-2-azidoethanone according to claim 1 which further comprises
   (a) reacting N-BOC-GLYCINE with dicyclohexylcarbodiimmide in methylene chloride,
   (b) reacting the product obtained in step (a) with the reduced 1-(2',5'-dimethoxyphenyl)-2-azidoethanone from claim 1 in the presence of 4,4'-dimethylaminopryidine, and
   (c) subjecting the product of step (b) to a polar or aprotic solvent.

5. A method according to claim 4 wherein the polar protic or aprotic solvent is selected from the group consisting of acetone/aq. HCl, HCl gas/MeOH, and HCl—EtOAc.

6. A method according to claim 3 wherein the haloacetylchloride is chloroacetylchloride.

7. A method according to claim 3 wherein the chlorinated solvent is methylenechloride.

8. The compound 1-(2',5'-dimethoxyphenyl)-2-azidoethanone.

* * * * *

UNITED STATES PATENT AND TRADEMARK OFFICE
CERTIFICATE OF CORRECTION

PATENT NO.   : 6,201,153 B1
DATED        : March 13, 2001
INVENTOR(S)  : Ray et al.

It is certified that error appears in the above-identified patent and that said Letters Patent is hereby corrected as shown below:

Title page,
Item [54], should read: -- SYNTHESIS OF MIDORINE HCL FROM A NOVEL INTERMEDIATE 1-(2',5'-DIMETHOXYPHENYL)-2-AZIDOETHANONE --

Column 1,
Line 1, should read: -- SYNTHESIS OF MIDORINE HCL FROM A --

Signed and Sealed this

Eighth Day of January, 2002

*Attest:*

JAMES E. ROGAN
*Attesting Officer*      *Director of the United States Patent and Trademark Office*